United States Patent [19]

Sugita et al.

[11] Patent Number: 4,595,470
[45] Date of Patent: Jun. 17, 1986

[54] PROCESS FOR THE PREPARATION OF BENZENE POLYCARBOXYLIC ACIDS

[76] Inventors: Nobuyuki Sugita, 3-4, Senmanda-cho, Shugakuin, Sakyo-ku, Kyoto-shi, Kyoto-fu, 606; Kiyoshi Kudo, 16, Nishikawa-cho, Nishikyogoku, Ukyo-ku, Kyoto-shi, Kyoto-fu, 615; Koichi Nagaoka, 3-58-30, Mutsukawa, Minami-ku, Yokohama-shi, Kanagawa-ken 232, all of Japan

[21] Appl. No.: 768,091

[22] PCT Filed: Dec. 14, 1984

[86] PCT No.: PCT/JP84/00600
§ 371 Date: Aug. 15, 1985
§ 102(e) Date: Aug. 15, 1985

[30] Foreign Application Priority Data

Dec. 15, 1983 [JP] Japan .................. 58-236888

[51] Int. Cl.⁴ .......................................... B01J 19/12
[52] U.S. Cl. .................................. 204/157.87
[58] Field of Search ........................... 204/158 R

[56] References Cited

U.S. PATENT DOCUMENTS 2,563,820  8/1951  Darragh et al. .............. 204/158 R

FOREIGN PATENT DOCUMENTS 1953971  6/1971  Fed. Rep. of Germany ...... 562/406

OTHER PUBLICATIONS

Chem. Abs., vol. 68 (17) 77910h.

*Primary Examiner*—Howard S. Williams
*Attorney, Agent, or Firm*—Wolder, Gross & Yavner

[57] ABSTRACT

A benzene polycarboxylic acid represented by the formula:

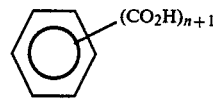

wherein n is an integer of 2 or 3, can be obtained under mild conditions with a high yield and with scarce formation of by-product by reacting a monochlorobenzene polycarboxylic acid represented by the formula:

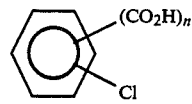

wherein n is an integer of 2 or 3, or its alkali metal salt with carbon monoxide in an aqueous solution of an alkali metal compound in the presence of a carbonylation catalyst with irradiation of ray of 340–400 nm, and subsequently acidifying the reaction solution.

4 Claims, No Drawings

PROCESS FOR THE PREPARATION OF BENZENE POLYCARBOXYLIC ACIDS

TECHNICAL FIELD

The present invention relates to a process for the preparation of benzene polycarboxylic acids.

BACKGROUND ART

With respect to the preparation of aromatic polycarboxylic acids, it has hitherto been proposed to synthetize benzoic acid and terephthalic acid respectively from chlorobenzene and 4-chlorobenzoic acid, for example, by the CO-insertion reaction at high temperature and under high pressure in the presence of a carbonylation catalyst such as cobalt carbonyl or by the phase-transfer catalyst method. However, it has not yet been reported that the desired product may be obtained with a high yield. Also it has not yet been reported that, for example, 4-chlorophthalic acid, 5-chlorotrimellitic and the like may be converted to the corresponding polycarboxylic acids such as trimellitic acid, pyromellitic acid and the like by the CO-insertion reaction.

Recently, studies on the photocarbonylation of chlorobenzene in the presence of a catalyst have been reported and moreover a study on the preparation of terephthalic acid by photocarbonylation of 4-chlorobenzoic acid in the presence of a cobalt carbonyl has been reported (Jean-Jacques Brunet, Christian Sidot & Paul Caubere, J. Org. Chem., 1983, 48, 1166–1171).

It was previously known in the art that, in the synthesis of aromatic carboxylic acids, the reaction becomes more difficult and the amount of by-products increases in accordance with the increase of the number of carboxyl groups.

It has now unexpectedly found that, by subjecting a monochloro-polycarboxylic acid to the photocarbonylation reaction in a homogeneous aqueous solution, the reaction proceeds smoothly and the reaction velocity becomes considerably faster than the corresponding velocity of the photocarbonylation reaction of 4-chlorobenzoic acid, and that by-product is scarcely formed.

DISCLOSURE OF INVENTION

The present invention relates to a process for the preparation of a benzene polycarboxylic acid represented by the formula:

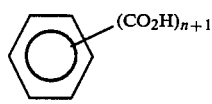

(wherein n is an integer of 2 or 3) which comprises reacting a monochlorobenzene polycarboxylic acid represented by the formula:

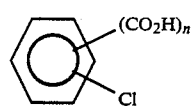

(wherein n is as hereinbefore defined) or an alkali metal salt thereof with carbon monoxide in an aqueous solution of an alkali metal compound in the presence of a carbonylation catalyst with irradiation of ray of 340–400 nm, and then acidifying the resultant reaction solution.

The present reaction can be carried out in a homogeneous solution under mild reaction conditions without the use of organic solvent and corrosive substance, and thus the present reaction is practically advantageous.

Preferred examples of the benzene polycarboxylic acids which may be prepared by the present invention include trimellitic acid (benzene 1,2,4-tricarboxylic acid), pyromellitic acid (benzene-1,2,4,5-tetracarboxylic acid) and the like.

Preferred examples of monochlorobenzene polycarboxylic acids include 4-chlorophthalic acid, 5-chlorotrimellitic acid and the like, and alkali metal salts thereof are exemplified by sodium salt, potassium salt, lithium salt and the like.

Preferred alkali metal compounds include, for example, alkali metal hydroxides such as sodium hydroxide, potassium hydroxide and the like, alkali metal carbonates such as sodium carbonate, potassium carbonates and alkali metal bicarbonates such as sodium bicarbonate, potassium bicarbonate and the like. The concentration of the aqueous solution of the alkali metal compound may be within a range of 0.5 to 10 (preferably 4–6) normal. When the concentration is not higher than 0.8 normal, the decrease of the yield of the desired product may sometimes be noted.

Examples of the carbonylation catalysts which may be used in the present invention include cobalt carbonyls (e.g. dicobalt octacarbonyl), nickel carbonyls, manganese carbonyls, iron carbonyls and the like. They may be used alone or in combination. The amount of the catalyst used may preferably, for example, 1/200 to $\frac{1}{2}$ mol on the basis of the carboxylic acid used as raw material.

The reaction according to the present invention may preferably be effected with irradiation of rays which correspond approximately to the maximum of the photoabsorption spectrum of the used catalyst, generally with irradiation of rays of 340–400 nm, preferably 350–370 nm.

According to the present invention, the reaction may preferably be effected at 40°–110° C. When the reaction is effected under low pressure (atmospheric pressure to 10 atm.), a reaction temperature of 60°–80° C. may be preferred. When the reaction temperature is 110° C. or higher, the dechlorination reaction of the starting substance may be accelerated and the yield of the desired polycarboxylic acid may be liable to decrease.

Although it is possible to carry out the reaction under a pressure between atmospheric pressure and high pressure (e.g. several hundred atm.), it is preferred from a practical point of view to use a pressure between atmospheric pressure and 20 atm. (e.g. from atmospheric pressure to 10 atm.). The reaction proceeds rapidly with a higher yield of the desired product when the reaction is carried out under increased pressure. In such a case, the use of a pressure between 2–20 atm, especially 2–10 atm is advantageous with respect to an effect and practicability.

Though the details of the reaction mechanism of the present invention are not yet clear, it is apparent that the present reaction proceeds under such conditions that formic acid is formed and exists in the reaction system because a small amount of formate is formed during the reaction.

For example, when the photocarbonylation reaction is effected by dissolving 4-chlorophthalic acid in an aqueous solution of sodium hydroxide (4-6N) and blowing carbon monoxide into the solution at a temperature of 60°-80° C. under a pressure of 1-10 atm, the reaction product consists mainly of the desired trimellitic acid, and by-product is scarcely formed except a small amount of formic acid. The reaction for obtaining pyromellitic acid from 5-chlorotrimellitic acid proceeds similarly as above.

After completion of the reaction, the desired product may be isolated and purified in a conventional manner. For example, the reaction solution after completion of the reaction is extracted with a solvent such as ether, and subjected to liquid chromatography, column chromatography, concentration, recrystallization, etc. in an appropriate combination, whereby the desired product may be isolated.

BEST MODE EMBODIMENTS FOR CARRYING OUT THE INVENTION

The following examples illustrate the invention.

EXAMPLE 1

The used reaction apparatus comprises an autoclave made of glass (Pyrex), having a volume of 60 ml and provided with a single fan stirrer, and a high pressure mercury lamp (500 W) capable of irradiating the autoclave from a distance of 30 cm. 25 ml of an aqueous solution of sodium hydroxide (5N), dicobalt octacarbonyl [0.5 mM of $Co_2(CO)_8$] and monosodium 4-chlorophthalate (3.6 mM) are put into the autoclave. Carbon monoxide (10 ml/min.) is introduced into the autoclave from the bottom under atmospheric pressure with irradiation of the light. The reaction mixture becomes transparent and homogeneous at about 45° C. The reaction is continued at a temperature of 65° C. for 8 hours with introduction of carbon monoxide.

After completion of the reaction, the reaction solution is adjusted to pH 3 with 20% aqueous solution of sulfuric acid and extracted with ether. The extract is treated with diazomethane in a conventional manner to convert the resultant trimellitic acid into its methyl ester, which is then assayed by gas chromatography under the following conditions: Apeazon L, ¾φ×1.5 m; 180° C.; carrier gas, nitrogen, 1 atm.

Analytical result: 0.88 mM of trimellitic acid and 2.0 mM of unreacted 4-chlorophthalic acid.

EXAMPLE 2

An aqueous solution of potassium hydroxide (25 ml; 5N), dicobalt octacarbonyl (0.5 mM), 4-chlorophthalic acid (3.6 mM) and phthalic acid (1.9 mM) are put into the reaction apparatus described in Example 1. Carbon monoxide (10-15 ml/min.) is introduced into the autoclave from the bottom at a reaction temperature of 65° C. During the photocarbonylation reaction for 8 hours, the reaction pressure is kept at 5 atm. After completion of the reaction, the reaction solution is treated in a similar manner to that described in Example 1, followed by analysis with gas chromatography.

Analytical result: 1.52 mM of trimellitic acid. 0.6 mM of unreacted 4-chlorophthalic acid and 1.6 mM of unreacted phthalic acid. No other by-product is detected.

EXAMPLE 3

An aqueous solution of sodium hydroxide (25 ml; 5N), dicobalt octacarbonyl (0.5 mM), 4-chlorophthalic acid (3.6 mM) and phthalic acid (1.9 mM) are charged into the reaction apparatus described in Example 1. Carbon monoxide is introduced into the reaction mixture (10-15 ml/min.) from the bottom of the autoclave at a reaction temperature of 65° C. During the photocarbonylation reaction effected for 8 hours, the reaction pressure is kept at 5 atm. The reaction solution is treated in a similar manner to that described in Example 1, followed by analysis with gas chromatography.

Analytical result: 1.6 mM of trimellitic acid, 1.4 mM of unreacted 4-chlorophthalic acid and 1.6 mM of unreacted phthalic acid. No by-product is detected.

EXAMPLE 4

An aqueous solution of sodium hydroxide (25 ml; 5N), dicobalt octacarbonyl (0.5 mM), sodium formate (29.4 mM), 4-chlorophthalic acid (3.6 mM) and phthalic acid (1.9 mM) are charged into the reaction apparatus described in Example 1 and treated in a similar manner to that described in Example 3.

Analytical result: 1.5 mM of trimellitic acid, 1.8 mM of unreacted 4-chlorophthalic acid and 1.6 mM of unreacted phthalic acid.

EXAMPLE 5

An aqueous solution of sodium hydroxide (25 ml; 5N), dicobalt octacarbonyl (0.5 mM) and 4-chlorophthalic acid (3.6 mM) are charged into the reaction apparatus described in Example 1 and treated in a similar manner to that described in Example 3 except the use of a reaction temperature of 110° C.

Analytical result: 1.11 mM of trimellitic acid, 1.22 mM of unreacted 4-chlorophthalic acid and 0.60 mM of unreacted phthalic acid.

EXAMPLE 6

An aqueous solution of potassium hydroxide (25 ml; 6N), dicobalt octacarbonyl (0.5 mM) and 5-chlorotrimellitic acid (5 mM) are charged into the reaction apparatus described in Example 1. Carbon monoxide is introduced into the reaction solution (10 ml/min) from the bottom of the autoclave at a reaction temperature of 70° C. The photo reaction is effected for 8 hours under atmospheric pressure. The reaction mixture is treated in a similar manner to that described in Example 1 to obtain 1 mM of pyromellitic acid.

EXAMPLE 7

A light condenser is provided in front of the light source of the reaction apparatus described in Example 1, and a similar reaction to that described in Example 3 is carried out to obtain 1.94 mM of trimellitic acid.

EXAMPLE 8

An aqueous solution of lithium hydroxide (25 ml; 5N), dicobalt octacarbonyl (0.49 mM) and 4-chlorophthalic acid (3.6 mM) are charged into the reaction apparatus described in Example 1, and a similar reaction to that described in Example 3 is carried out to obtain 1.28 mM of trimellitic acid.

We claim:

1. A process for the preparation of a benzene polycarboxylic acid represented by the formula:

wherein n is an integer of 2 or 3, which comprises reacting a monochlorobenzene polycarboxylic acid represented by the formula:

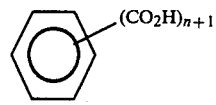

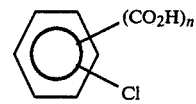

wherein n is as hereinbefore defined, or an alkali metal salt thereof which carbon monoxide in an aqueous solution of an alkali metal compound in the presence of a carbonylation catalyst with irradiation of ray of 340–400 nm, and then acidifying the resultant reaction solution.

2. A process as claimed in claim 1, characterized in that the reaction is effected in a homogeneous system.

3. A process as claimed in claim 1, characterized in that the reaction is effected in the presence of an alkali metal salt of formic acid.

4. A process as claimed in claim 1, characterized in that the reaction is effected under a pressure of 2–20 atm.

* * * * *